(12) United States Patent
Levine

(10) Patent No.: US 8,005,546 B1
(45) Date of Patent: Aug. 23, 2011

(54) REMOTE FOLLOW-UP AUTOMATICITY WITH INTELLIGENT DATA DOWNLOAD RESTRICTIONS

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1042 days.

(21) Appl. No.: 11/838,781

(22) Filed: Aug. 14, 2007

(51) Int. Cl.
*A61N 1/37* (2006.01)
*A61N 1/08* (2006.01)

(52) U.S. Cl. .................. 607/32; 607/30; 607/31

(58) Field of Classification Search ........... 607/30–32; 600/518
See application file for complete search history.

(56) References Cited

U.S. PATENT DOCUMENTS

| | | | | |
|---|---|---|---|---|
| 6,247,474 | B1 * | 6/2001 | Greeninger et al. | 128/899 |
| 7,801,612 | B2 * | 9/2010 | Johnson et al. | 607/32 |
| 2006/0247709 | A1 | 11/2006 | Gottesman et al. | |
| 2007/0250130 | A1 * | 10/2007 | Ball et al. | 607/32 |

FOREIGN PATENT DOCUMENTS

WO 2006115888 A1 11/2006

* cited by examiner

*Primary Examiner* — Carl H. Layno
*Assistant Examiner* — Tammie K Heller

(57) ABSTRACT

An implanted device is equipped with a flag that indicates to a remote monitoring unit that an event such as a patient medical emergency or device failure has occurred. The remote monitoring unit is configured in some embodiments to maintain a low power communication link with the implanted device when they are within range. When the flag indicates an event has occurred, the remote monitoring unit quickly downloads sensed data collected by the implanted device and transfers it over a network so that it can be utilized by a medical practitioner. The remote monitoring unit is further configured in some embodiments to query the implanted device at regular intervals. The remote monitoring unit may read a subset of the data stored by the implanted device and, based on that data, determine whether to complete a full or partial download.

13 Claims, 7 Drawing Sheets

REMOTE FOLLOW-UP AUTOMATICITY WITH INTELLIGENT DATA DOWNLOAD RESTRICTIONS

FIELD OF THE INVENTION

The present invention generally relates to an implantable pulse generator or implantable cardiac stimulation devices. The present invention more particularly concerns a system for efficiently downloading data collected by an implanted pulse generator to a remote monitoring unit.

BACKGROUND OF THE INVENTION

Implantable cardiac pulse generators such as implantable cardiac stimulation devices (IPGs) may take the form of implantable cardioverter-defibrillators that utilize unique and rapid stimulation rates or high energy shocks to treat accelerated or chaotic rhythms of the heart in an effort to restore a normal heart rhythm. IPGs can also include pacemakers that provide low voltage stimulation to regulate the heart rate in the setting of a bradycardia. In addition to providing therapeutic stimulation, these IPGs include sensing circuits that sense electrical signals generated by the heart indicative of cardiac activity and memory device to store these sensed signals and data. IPGs are typically also configured to transmit stored signals and data to external devices or programmers in order to aid a diagnosis by a physician or clinician. For the purpose of this patent, an IPG represents any implantable medical device capable of monitoring one or more physiologic functions and/or delivering therapy. As such, in addition to cardiac pacemakers and cardioverter-defibrillators which are well established in the art, this also includes neurologic stimulation devices, gastric stimulation devices, implantable monitors including cardiac monitors, glucose monitors and others.

Historically, the transfer of data from the IPG to the programmer or other device was performed either in the hospital or the physician's office. Increasingly, the transfer of this data from the implantable device to an external device accessible by a physician is done in locations outside of a clinic, hospital, or other traditional medical setting. For example, a patient having an IPG may also have a remote monitoring unit (RMU) in their home that automatically communicates with the IPG to wirelessly download data acquired by the IPG. Data acquired by the RMU may be transferred over a network to a remote server so that it is accessible to a physician or a clinician at a remote medical site.

However, RMUs fail to handle many dangerous events and the general transfer of data efficiently. For example, a typical RMU located in a patient's home may operate by downloading information obtained and stored on the IPG at regular intervals. However, an event (e.g., a patient's medical condition) may occur shortly after the previous download and this event would not be acquired by the system until the next scheduled download. In the case that the event represents a problem with the IPG or a patient emergency, the proper medical professional may not be alerted quickly when another scheduled download is not for some time. This may put the patient at risk when a problem is being experienced and they are unable to either detect or inform a physician or emergency medical technician themselves.

One current solution to this problem used with some RMUs is to increase the frequency at which data transfers occur. If the RMU downloads information from the IPG more frequently, then the average time between an event and data collection will decrease. However, the frequent transfer of information from the implanted device and the monitoring system may reduce the battery life of the IPG because of the increased power requirements of the more frequent wireless transfer of information. When there is no meaningful event to report, this excessive transfer of information is inefficient and needlessly reduces battery life as well as potentially overloads the memory of the server or the RMU. Additionally, the drain on the battery becomes worse as the time between transfers decreases, forcing a trade-off with this solution between device life and safe monitoring of the patient. Even in circumstances where the download frequency has not been increased, valuable battery power may be used to implement preplanned downloads that contain information of limited value. Generally, implantable cardiac stimulation devices that have download capability are programmed to download at regular intervals. However, some patients may have relatively stable cardiac conditions such that the information being downloaded provides no real new information to the treating physician. In this circumstance, battery power is being consumed to provide information of limited value. Conserving battery power is, of course, of great concern with implanted devices as IPG replacement due to battery depletion typically involves an invasive medical procedure.

Thus, there is a need in the art for a system that more efficiently provides information obtained by an IPG to a RMU. There is a need in the art for a system that is able to quickly alert a physician or emergency medical technician to the occurrence of a major event, while limiting downloads and drain on battery power when the downloaded information does not warrant the power expense.

SUMMARY OF THE INVENTION

According to one embodiment, an implantable pulse generator is configured to sense cardiac activity and to provide therapeutic electrical stimulation. The IPG advantageously provides for the download of sensed data only when there has been a significant change in the data in order to conserve the battery life of the IPG and minimize data overload to the system. The IPG comprises a wireless transceiver configured to establish a communications link with an external computing device and to broadcast data to and receive data from the external computing device. The IPG further comprises at least one sensor configured to sense cardiac activity including the activity of a patient's heart and the performance of the implanted pulse generator. A memory is configured to store data indicative of the sensed cardiac activity and further comprises a download schedule including a plurality of scheduled downloads. A processor of the IPG is configured to analyze the stored data according to the download schedule in order to determine whether a significant change has occurred. The processor is further configured to induce the wireless transceiver to transmit the stored data to the external computing device when it is determined that a significant change has occurred. The processor is configured to not undertake one of the plurality of scheduled downloads when it is determined that a significant change has not occurred.

According to another embodiment, a cardiac monitoring system is provided including an implantable cardiac stimulation device and a monitoring device. The implantable cardiac stimulation device has a memory and a communications link. The implantable cardiac stimulation device provides therapy to the patient's heart in accordance with a plurality of programmed parameters, senses the performance of the device and the patient's heart, and stores signals indicative thereof in the memory. The implantable cardiac stimulation device categorizes the signals based upon pre-selected criteria. The monitoring device includes a first communications link that is capable of communicating with the implantable cardiac stimulation device. The monitoring device periodically queries the implantable cardiac stimulation device for update information about the performance of the implantable cardiac stimulation device or the patient's heart. The implantable cardiac stimulation device is configured to transmit update information generated from the stored signals in response to receiving the periodic query from the monitoring device only when the implantable cardiac stimulation device has categorized the signals based upon the pre-selected criteria as being important enough to warrant transmission.

According to yet another embodiment, a method of controlling a computing device that is configured to communicate with an implantable device in order to read a first set of data from the implantable device is provided. The method allows for the immediate download of data relating to an emergency event detected by the implantable device and for the generation of an alarm signaling the emergency event. The method comprises the computing device establishing a wireless communications link with the implantable device and reading an indicator in the implantable device. The computing device downloads the first set of data when the indicator indicates that a first event has occurred. The computing device then resets the indicator in the implantable device so that it indicates that that the first set of data has been downloaded. The method further comprises generating an alarm when the indicator indicates that the first event has occurred.

Accordingly, different embodiments allow for the efficient control and monitoring of an IPG or an implantable cardiac stimulation device so that a data download is attempted to an RMU as soon as the IPG is in proximity of an RMU after an emergency event has occurred. Downloads otherwise occur in some embodiments according to a schedule, but scheduled downloads may be canceled if it is determined that the data stored in the IPG has not changed significantly. In some embodiments, alarms are generated by the RMU to notify those nearby or medical professionals at remote locations in order to provide assistance when an emergency event occurs.

Throughout the disclosure, reference is made to an IPG in order to describe certain aspects of the invention. However, a skilled artisan will understand that some or all of the features described herein may be applied to other implantable devices. Specifically, other implantable devices that are capable of detecting physiologic events and/or monitoring their own behavior, and that are capable of transferring such data to a programmer in a medical facility or to an RMU outside of a medical facility, may be used according to certain embodiments of the invention. Accordingly, the disclosure provided here may apply not only to sensed data indicative of the activity of the heart, but to any sensed data indicative of a patient's medical condition. Furthermore, the disclosure may apply to devices that monitor activity or device performance without providing any type of therapy, such as electrical stimulation therapy.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
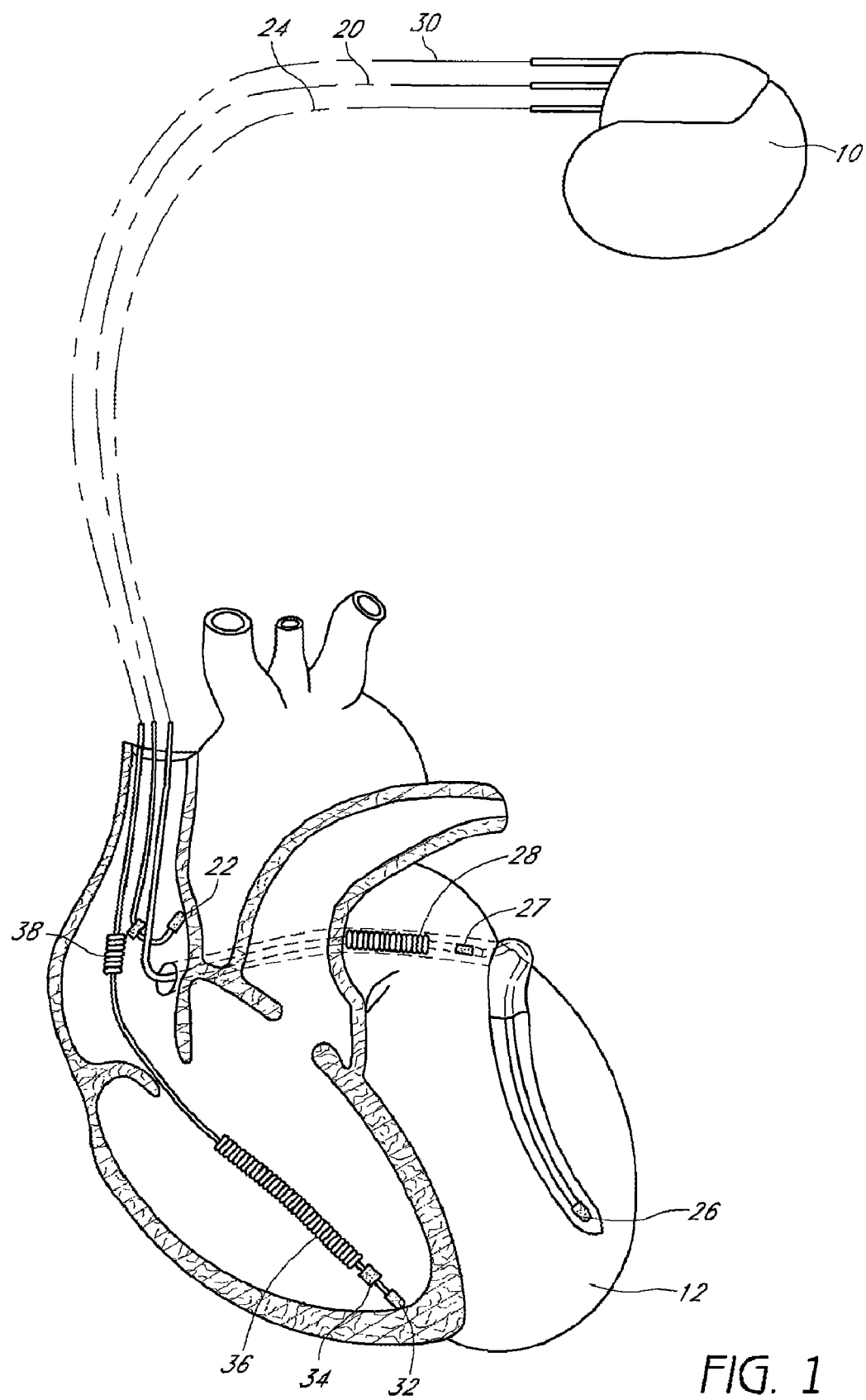
FIG. 1 is a simplified diagram illustrating an implantable stimulation device in electrical communication with three leads implanted into a patient's heart for delivering multi-chamber stimulation and shock therapy, according to an embodiment of the invention.

According to an embodiment shown in FIG. 1, there is an implanted pulse generator throughout IPG 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the IPG 10 is coupled to an implantable right atrial lead 20 having an atrial tip electrode 22, which typically is implanted in the patient's right atrium, often in the atrial appendage but not limited to this position.

To sense left atrial and ventricular cardiac signals and to provide left chamber pacing therapy, the IPG 10 is coupled to a "coronary sinus" lead 24 designed for placement in the "coronary sinus region" via the coronary sinus is for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using a left ventricular tip electrode 26, left atrial pacing therapy using a left atrial ring electrode 27, and shocking therapy using a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The IPG 10 is also shown in electrical communication with the patient's heart 12 by way of an implantable right ventricular lead 30 having, in this embodiment, a right ventricular tip electrode 32, a right ventricular ring electrode 34, a right ventricular (VR) coil electrode 36, and an SVC coil electrode 38. Typically, the right ventricular lead 30 is transvenously inserted into the heart 12 so as to place the right ventricular tip electrode 32 in the right ventricular apex so that the VR coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. The right ventricular tip electrode 32, however can be placed virtually any place in the right ventricle such as the mid-septal region or the right ventricular outflow tract and is not limited to the right ventricular apex.

While IPG 10 is shown in this embodiment as having certain leads, according to other embodiments IPG 10 may additionally or alternatively comprise other sensors and leads. For example, IPG 10 may sense the electrical activity of a patient's heart 12 utilizing a multiple electrode lead having 8, 16, 32 or some other number of electrodes spatially distributed across at least one chamber of the heart 12. In some embodiments other sensors may be used such as pressure sensors, or the like.

Figure 2:
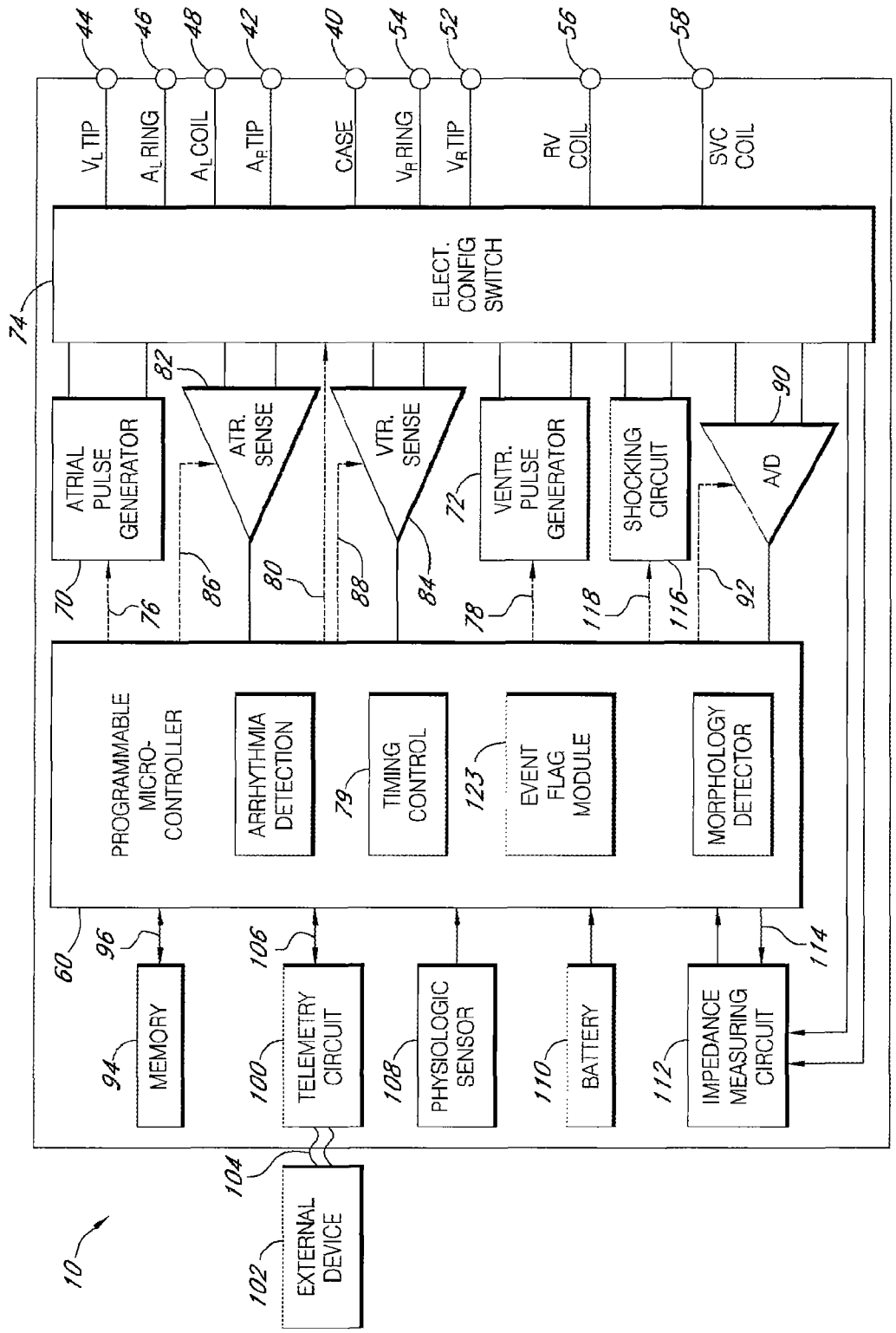
FIG. 2 is a functional block diagram of a multi-chamber implantable stimulation device illustrating the basic elements of a stimulation device, which can provide cardioversion, defibrillation, and pacing stimulation in four chambers of the heart, according to an embodiment of the invention.

According to an embodiment illustrated in FIG. 2, a simplified block diagram is shown of the multi-chamber IPG 10, which is capable of treating both fast and slow arrhythmias with stimulation therapy, such as cardioversion, defibrillation, and pacing stimulation. While a particular multi-chamber device is shown, this is for illustration purposes only, and one of skill in the art could readily duplicate, eliminate, or disable the appropriate circuitry in any desired combination to provide a device capable of treating the appropriate chamber(s) with cardioversion, defibrillation, and pacing stimulation. In certain embodiments of the invention, an implanted device may be utilized having appropriate circuitry for sensing the electrical activity of the heart without circuitry for providing stimulation therapy.

The housing 40 for the IPG 10, shown schematically in FIG. 2, is often referred to as the "can", "case", or "case electrode" and will act as the return electrode for all "unipolar" modes. The housing 40 can further be used as a return electrode alone or in combination with one or more of the coil electrodes, 28, 36, and 38, for shocking purposes. The housing 40 further comprises a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector comprises a right atrial tip terminal (AR TIP) 42 adapted for connection to the atrial tip electrode 22.

To achieve left chamber sensing, pacing, and shocking, the connector comprises a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively.

To support right chamber sensing, pacing, and shocking, the connector further comprises a right ventricular tip terminal (VR TIP) 52, a right ventricular ring terminal (VR RING) 54, a right ventricular shocking terminal (VR COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the IPG 10 is a programmable microcontroller 60, which controls the various modes of stimulation therapy. As is well known in the art, the microcontroller 60 typically comprises a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 comprises the ability to process or monitor input signals (data) as controlled by a program code stored in a designated block of memory. The details of the design and operation of the microcontroller 60 are not critical to the present invention. Rather, any suitable microcontroller 60 can be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, can include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further comprises timing control circuitry 79 that is used to control the timing of such stimulation pulses (e.g., pacing rate, atrio-ventricular (AV) delay, inter-atrial conduction (A-A) delay, or inter-ventricular conduction (V-V) delay, etc.) as well as to keep track of the timing of refractory periods, PVARP intervals, noise detection windows, evoked response windows, alert intervals, marker channel timing, etc., which is well known in the art.

The switch 74 comprises a plurality of switches for connecting the desired electrodes to the appropriate I/O circuits, thereby providing electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 can also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, can include dedicated sense amplifiers, multiplexed amplifiers, or shared amplifiers. The switch 74 determines the "sensing polarity" of the cardiac signal by selectively closing the appropriate switches, as is also known in the art. In this way, the clinician can program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the IPG 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the IPG 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation, which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram (EGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection can occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The lowest value at which there is consistent capture is known as the capture threshold. Thereafter, a safety margin or a working margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the IPG 10 to suit the needs of a particular patient. Such operating parameters define, for example, pacing pulse amplitude, pulse duration, electrode polarity, rate, sensitivity, automatic features, arrhythmia detection criteria, and the amplitude, waveshape, and vector of each shocking pulse to be delivered to the patient's heart 12 within each respective tier of therapy. An embodiment of the invention senses and stores a relatively large amount of data (e.g., from the data acquisition system 90), which data can then be used for subsequent analysis to guide the programming of the IPG 10.

Advantageously, the operating parameters of the IPG 10 can be non-invasively programmed into the memory 94 through a telemetry circuit 100 in telemetric communication with the external device 102, such as a remote monitoring unit, programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the IPG 10 (as contained in the microcontroller 60 or memory 94) to be sent to the external device 102 through an established communication link 104.

In the preferred embodiment, the IPG 10 further comprises a physiologic sensor 108, commonly referred to as a "rate-responsive" sensor because it is typically used to adjust pacing stimulation rate according to the exercise state of the patient. However, the physiological sensor 108 can further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the IPG 10, it is to be understood that the physiologic sensor 108 can also be external to the IPG 10, yet still be implanted within or carried by the patient. A common type of rate responsive sensor is an activity sensor, such as an accelerometer or a piezoelectric crystal, which is mounted within the housing 40 of the IPG 10. Other types of physiologic sensors are also known, for example, sensors that sense the oxygen content of blood, respiration rate and/or minute ventilation, pH of blood, ventricular gradient, etc. However, any sensor can be used that is capable of sensing a physiological parameter that corresponds to the exercise state of the patient. The type of sensor used is not critical and is shown only for completeness.

The stimulation device additionally comprises a battery 110, which provides operating power to the circuits shown in FIG. 2, including telemetry circuit 100. For the IPG 10, which employs shocking therapy, the battery 110 is capable of operating at low current drains for long periods of time, and then be capable of providing high-current pulses (for capacitor charging) when the patient requires a shock pulse. The battery 110 also has a predictable discharge characteristic so that elective replacement time can be detected. Accordingly, the IPG 10 preferably employs lithium/silver vanadium oxide batteries.

The IPG 10 further comprises magnet detection circuitry (not shown), coupled to the microcontroller 60. It is the purpose of the magnet detection circuitry to detect when a magnet is placed over the IPG 10, which magnet can be used by a clinician to perform various test functions of the IPG 10 and/or to signal the microcontroller 60 that the external programmer 102 is in place to receive or transmit data to the microcontroller 60 through the telemetry circuits 100. However, the magnet detection circuitry is not necessary to establish a communication link 104 according to some embodiments. In certain embodiments, the magnetic detection circuitry may trigger specific behavior such as signaling the status of the battery 110 or storing an electrogram.

As further shown in FIG. 2, the IPG 10 is shown as having an impedance measuring circuit 112, which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode can be used.

In the case where the IPG 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least one shocking electrode but potentially more shocking electrodes, and as shown in this embodiment, selected from the left atrial coil electrode 28, the RV coil electrode 36, and/or the SVC coil electrode 38. As noted above, the housing 40 can act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to conserve battery life), and/or synchronized with an R-wave and/or pertaining to the treatment of tachycardia. Defibrillation shocks are generally of moderate to high energy level (i.e., corresponding to thresholds in the range of 5-40 Joules), and pertaining to the treatment of fibrillation. Accordingly, the microcontroller 60 is capable of controlling the synchronous or asynchronous delivery of the shocking pulses.

Microcontroller 60 of the IPG 10 further comprises an event flag module 123. As discussed below, flag 123 can be set by an external device 102 in order to indicate that the external device 102 has downloaded data contained in the memory 94 of microcontroller 60. When the external device 102 sets the flag 123, the flag 123 may correspond to an enabled condition and in some embodiments a logical "1" value. The microcontroller 60 is further configured in some embodiments to set the flag 123 when an event has occurred to a disabled condition, corresponding in some embodiments to a logical "0" value. The use of a particular electrical value or signal for each condition of the flag may, of course, be varied depending on a particular design choice. In some embodiments, flag 123 includes multiple flags corresponding to a variety of indicators for indicating different events or conditions. As will be explained in more detail below, the flag 123 may therefore be used in some embodiments to indicate when a remote monitoring unit 62 should download data from the IPG 10.

Figure 3:
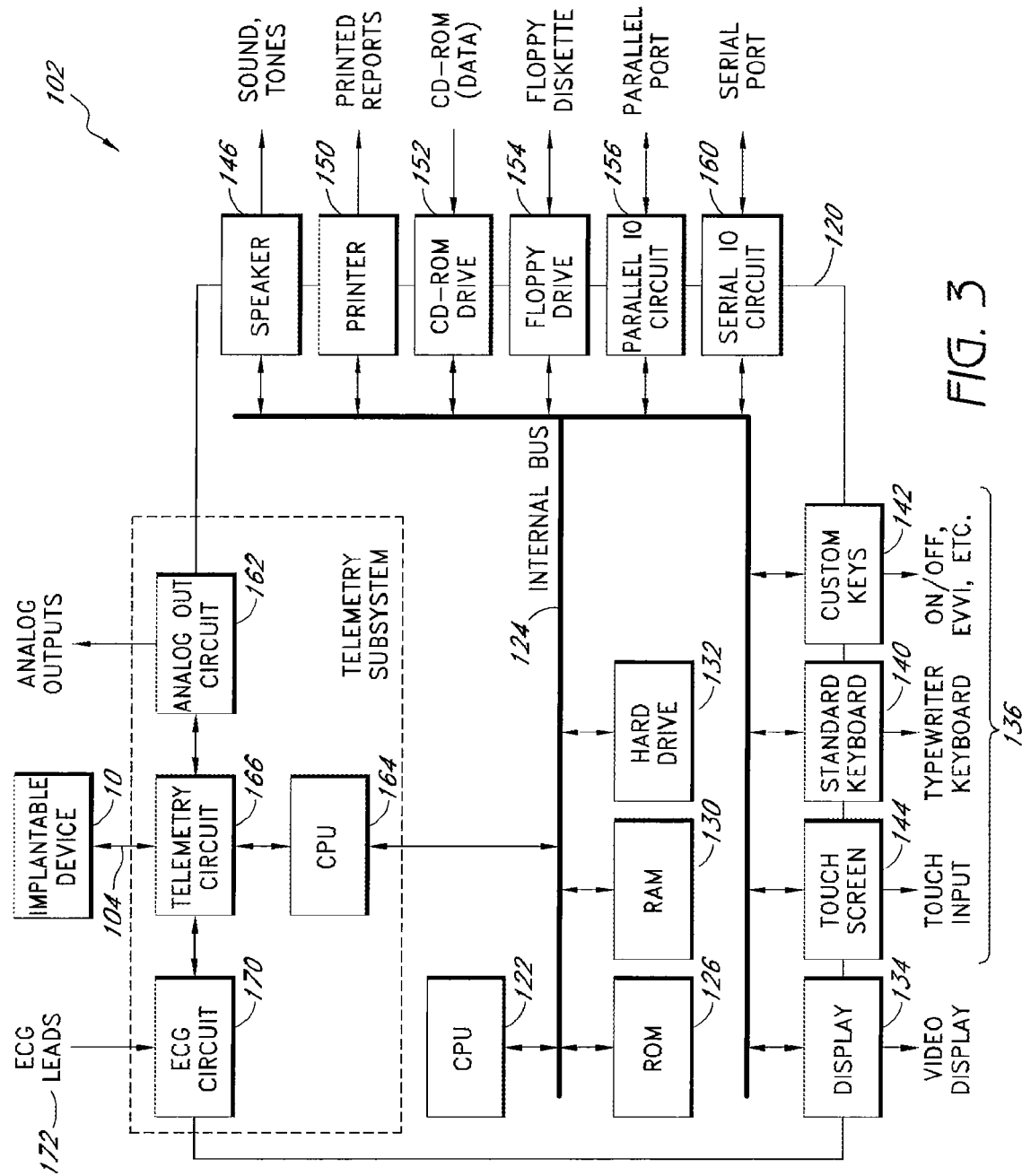
FIG. 3 is a functional block diagram of an external programmer device, according to an embodiment of the invention.

FIG. 3 is a functional block diagram of one embodiment of the external device 102, such as a physician's programmer or remote monitoring unit. The external device 102 comprises a CPU 122 in communication with an internal bus 124. The internal bus 124 provides a common communication link and power supply between various electrical components of the external device 102, such as the CPU 122. The external device 102 also comprises memory and data storage such as ROM 126, RAM 130, and a hard drive 132 commonly in communication with the internal bus 124. The ROM 126, RAM 130, and hard drive 132 provide temporary memory and non-volatile storage of data in a well known manner. In one embodiment, the ROM 126, RAM 130, and hard drive 132 can store control programs and commands for upload to the IPG 10 as well as operating software for display of data received from the IPG 10. It will be appreciated that in certain embodiments alternative data storage/memory devices, such as flash memory, can be included or replace one or more of the ROM 126, RAM 130, and hard drive 132 without detracting from the spirit of the invention.

The external device 102 also comprises a display 134. The display 134 is adapted to visually present graphical and alphanumeric data in a manner well understood in the art. The external device 102 also comprises input devices 136 to enable a user to provide commands and input data to the external device 102. In one embodiment, the input devices 136 include a keyboard 140, a plurality of custom keys 142, and a touch screen 144 aspect of the display 134. The keyboard 140 facilitates entry of alphanumeric data into the external device 102. The custom keys 142 are programmable to provide one touch functionality of predefined functions and/or operations. The custom keys 142 can be embodied as dedicated touch keys, such as associated with the keyboard 140 and/or predefined areas of the touch screen 144. In this embodiment, the external device 102 also comprises a speaker 146 and a printer 150 in communication with the internal bus 124. The speaker 146 is adapted to provide audible alert send signals to a user. The printer 150 is adapted to provide a printed readout of information from the external device 102.

In this embodiment, the external device 102 also comprises a CD drive 152 and a floppy drive 154 which together provide removable data storage. In this embodiment, the external device also comprises a parallel input-output (10) circuit 156, a serial 10 circuit 160, and an analog output circuit 162. In certain embodiments, the external device 102 also comprises a USB interface. In some embodiments, the external device 102 may also comprise an industry standard interface compatible with other portable storage devices such as a flash memory device. These circuits 156, 160, 162 provide a variety of communication capabilities between the external device 102 and other devices in a manner well understood in the art.

The external device 102 also comprises an electrocardiogram (ECG) circuit 170 in communication with a plurality of ECG leads 172. The ECG circuit 170 and the ECG leads 172 obtain electrical signals from the surface of a patient's body and configure the signals for display as an ECG waveform on the display 134 of the external device 102.

The external device 102 also comprises a telemetry CPU 164 and a telemetry circuit 166, which establish the telemetric link 104 in cooperation with the IPG 10. The telemetric link 104 comprises a bidirectional link to enable the external device 102 and the IPG 10 to exchange data and/or commands. As previously noted, the establishment of the telemetric link 104 is in certain embodiments facilitated by a wand or programmer head, which is placed in proximity to the IPG 10. The wand or programmer head facilitates establishment of the telemetric link 104 by placing an antenna structure in a closer proximity to the IPG 10 to facilitate conduction of transmitted signals to the external device 102.

The telemetric link 104 can in some embodiments comprise a variety of communication protocols appropriate to the needs and limitations of a given application. In certain embodiments, the telemetric link 104 comprises radio frequency (RF) telemetry. In one particular embodiment, the telemetric link 104 comprises a frequency modulated digital communication scheme wherein logic ones are transmitted at a first frequency A and logic zeros are transmitted second frequency B. As the IPG 10 is powered by a battery having limited capacity and in certain embodiments the external device 102 is powered by line voltage, e.g., not subject to the stringent power limitations of the IPG 10, the bidirectional telemetric link 104 can proceed in an asymmetric manner. For example, in one embodiment, a transmission power and data rate from the external device 102 to the IPG 10 via the telemetric link 104 can proceed at higher power levels and/or higher data transmission rates than the reciprocal data rates and transmission power from the IPG 10 to the external device 102. The telemetry circuit 100 of the IPG 10 as well as the telemetry circuit 166 and CPU 164 of the external device 102 can select or be adjusted to provide a desired communication protocol and transmission power.

Figure 4:
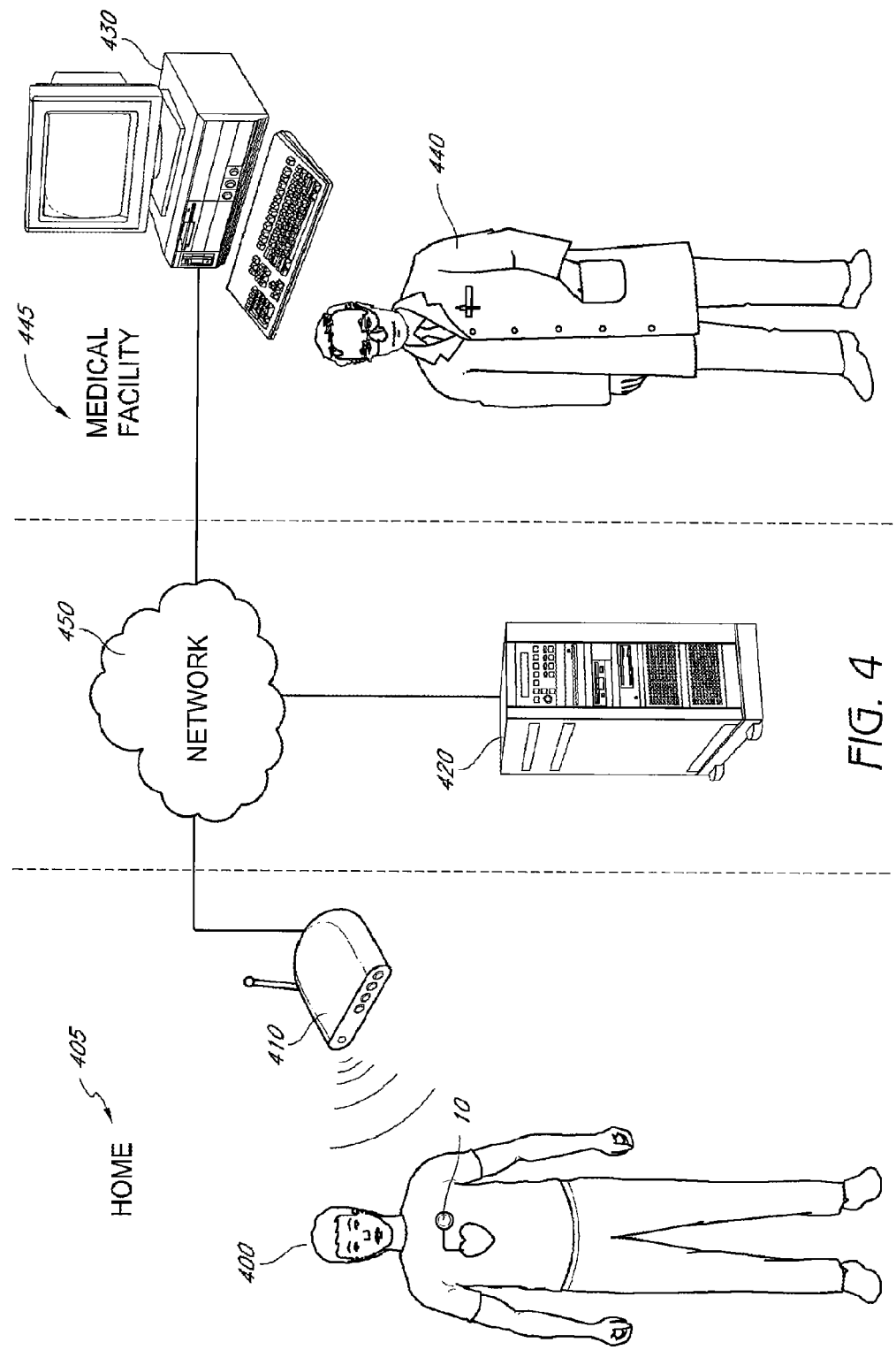
FIG. 4 is a diagram of a system for connecting an implanted cardiac device to a computing station at a medical facility, according to an embodiment of the invention.

FIG. 4 shows an example of a remote monitoring system comprising a home location 405 and a medical facility 445 connected over a network 450. The home location includes a patient 400 with an implanted pulse generator 10 which in this implementation is an implanted cardiac stimulation device. IPG 10 collects data indicative of the activity of the heart of patient 400, as described above with reference to FIGS. 1 and 2. Home location 405 further includes a remote monitoring unit 410. RMU 410 may be an external device 102 as described above with reference to FIG. 3, but may be specifically adapted for use in a home, office, or other location outside a typical medical setting. RMU 410 periodically communicates with the IPG 10 implanted in the patient 400 in order to upload cardiac data collected by the IPG 10.

Data collected by the IPG 10 and transferred to the RMU 410 may be transferred over a network 450. In some embodiments, network 450 corresponds to the Internet. In other embodiments, network 450 comprises a local area network. For example, network 450 may comprise a local area network in a hospital or other medical facility. In still other embodiments, network 450 corresponds to a direct connection between computing devices, a wireless network, or the like.

Data transferred over the network 450 may further be stored on a server 420. Server 420 may comprise any computing device capable of communicating over network 420, such as a personal computer or blade server. In some embodiments, server 420 may store and operate a hospital or medical database system that contains patient data and records. The server may include software that allows access to the database system by certain medical professionals 440 and by the RMU 410.

A monitoring station 430 located at medical facility 445 accesses the data stored on server 420 over the network 450. In some other embodiments, monitoring station 430 may download patient data directly from the RMU 410. Monitoring station 430 obtains the patient data stored on server 420 and displays the data to a physician or clinician 440. A physician or clinician 440 may use monitoring station 430 in order to view some or all the patient data according to the display software of the monitoring station 430. Monitoring station 430 may have some or all of the same functionality of the external device 102 shown in FIG. 3. For example, monitoring station 430 may not include a telemetry circuit 166 in some embodiments. In some embodiments, monitoring station 430 further comprises other features, such as an alarm or ethernet port.

While the system shown in FIG. 4 conveniently allows for the transfer of information from an IPG 10 to a medical provider without requiring the patient 400 to travel to the medical facility 445, the transfer of information from implanted IPG 10 to RMU 410 requires more power consumption than the standard operation of implanted IPG 10 because the transmitter must be powered. As more data is transferred from implanted IPG 10, and at a higher frequency, the amount of power required by this process increases. As that occurs, the useful life of the implanted IPG 10 decreases. When the batteries are near or at their depleted levels the user must have them replaced, which may involve invasive surgery. Thus, it is desired that the battery life of the IPG 10 be extended as much as possible.

However, the less frequent download of data sensed by the implanted IPG 10 increases the likelihood that a major event, such as a patient medical condition or a device failure, will not be detected by the remote monitoring unit 410 and the relevant information sent to clinician or physician 440 until it is too late to provide patient 400 with the necessary treatment. Current systems may have this problem, because they operate on periodic cycles of set times. Thus, whether data is downloaded once per week, once per day, or once per hour, there is a significant amount of time between downloads. If a patient 400 experiences a medical emergency or there is a device failure shortly after a download occurs, then the next scheduled download will not occur for a relatively long time. If the patient 400 is not aware of this event or is unable to contact a physician 440 or other emergency medical technician for assistance, the necessary medical attention may not be received.

According to some embodiments, these problems related to battery life and critical events are substantially reduced. For example, according to some embodiments, the battery life of an IPG 10 may be extended by only downloading information that reflects a significant change, or only downloading information related to the occurrence of an event. When the time period for the scheduled download occurs and there is not significant information to download, the download can be limited so as to minimize unnecessary battery depletion.

Alternatively, in order to provide efficient and fast assistance during a significant event, a system is provided for causing the IPG 10 to transfer information to the RMU 410 after the occurrence of an event and as soon as the implanted IPG 10 is in range of the RMU 410 rather than waiting for a download period. Thus, as will be described in more detail below, the more efficient and intelligent monitoring of data collected by an IPG 10 is achieved according to some embodiments of the current invention.

Figure 5:
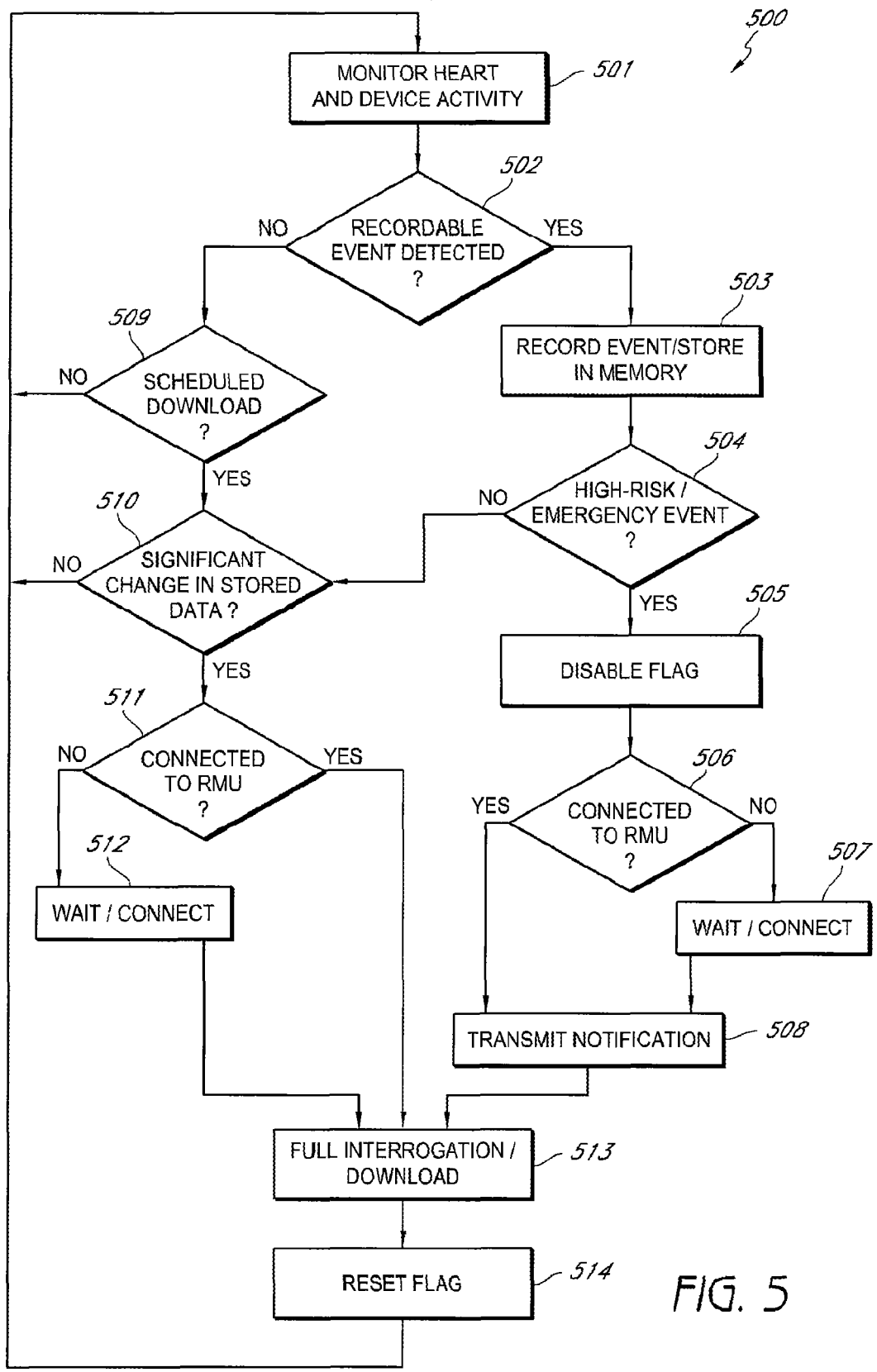
FIG. 5 is a flow chart describing a method for intelligently controlling the recording and transfer of data from an implantable pulse generator based upon the occurrence of a significant event or change in stored data, according to one embodiment of the invention.

FIG. 5 is a flow chart describing a process 500 for the efficient collection and analysis of data sensed by an IPG 10 according to one embodiment. The process 500 may be utilized, for example, by an IPG 10 when sensing data indicative of the activity of a patient's heart 12 and communicating with an RMU 410.

The process 500 begins at state 501 where the IPG 10 monitors heart and device activity. For example, the IPG 10 may monitor the electrical activity of the patient's heart 12 as sensed by VL tip electrode 26, the VR tip electrode 32, or AR tip electrode 22. IPG 10 may further sense data such as pressure data, movement data, impedance measurements, battery life, or the like. Based on the monitored heart and device activity, the IPG 10 may determine the occurrence of an event. An event may include a medical event, such as an arrhythmia, or the like. An event may also include a device event such a dislodged or damaged lead or a low battery.

The process 500 continues to decision state 502. At decision state 502 the IPG 10 determines if a recordable event has been detected. In some embodiments, parameters determining what constitutes a recordable event are programmed, for example, by a physician using an external programmer 102. In some embodiments, any event detected by IPG 10 is recordable. In other embodiments only a limited number of events are recorded to preserve limited memory space. If it is determined that its decision state 502 that a recordable event has occurred, then the process 500 proceeds to state 503. Otherwise the process 500 continues to state 509.

At 503, the detected event is recorded and stored in the memory 94 of the IPG 10. In some embodiments, data collected by the IPG 10 is stored in the memory 94 for predetermined amount of time before being erased. In such embodiments, when it is determined at decision state 502 a recordable event has occurred, then the IPG 10 may prevent data representing that event from being erased from memory 94. In some embodiments, certain events may be detected at their outset and recorded and stored in memory 94 only after they have been detected. In some embodiments, only an indicator that an event has occurred is stored, rather than the data surrounding the event. For example, a low battery event might cause an indication of the low battery to be stored rather than measured data. Similarly, the incident of a capture threshold may be recorded rather than measured amplitude.

The process 500 then continues to decision state 504. At decision state 504 it is determined whether the recorded event constitutes a high risk or emergency event. A high risk or emergency event may be determined by the IPG 10 based on predetermined factors. In some embodiments, these factors are programmed using an external programmer 102 by a physician. High risk or emergency events may represent, for example, a medical condition that requires immediate medical attention in order to prevent patient injury or death such as the occurrence of a new type of heart arrhythmia or the occurrence of particularly severe or frequent heart arrhythmias. A high risk event may also correspond to a device malfunction or condition requiring immediate medical attention, such as a very low battery life or a broken or dislodged lead. If it is determined at decision state 504 that the recorded event is not a high risk or emergency event, then the process 500 continues to state 509. If it is determined at decision state 504 that the recorded event constitutes a high risk or emergency event, then the process 500 continues to state 505.

At state 505, the IPG 10 disables the flag of the event flag module 123. Although in the description of process 500 only one flag is utilized, it is understood that in other embodiments multiple flags may be used by IPG 10. For example, certain flags may indicate different types of conditions. For example, one flag may indicate a device malfunction and another flag may indicate a medical condition. In some embodiments, a number of flags may be used and may be programmed by a physician using an external programmer 102. The flag disabled at state 505 signifies that at least one type of high risk or emergency event has occurred since the last data download by the RMU 410.

The process 500 then continues to decision state 506. At decision state 506, it is determined whether the IPG 10 is connected to RMU 410 over a wireless communications link 104. If the IPG 10 is in range of the RMU 410 and is connected, then the process 500 proceeds to state 508. If the RMU 410 is not connected to the IPG 10, then the process 500 continues to state 507. At state 507 of the process 500, the IPG 10 waits and attempts to connect with the RMU 410. For example, the IPG 10 may wait until the RMU 410 is within range. For example, a patient having an IPG 10 may have an RM 410 located in his or her home. If the patient is away from the home when an event is detected, then the IPG 10 will connect with the RMU 410 when the patient returns home and is within range of the RMU 410 such that the IPG senses the proximity of the RMU, e.g. by receiving a polling signal from the RMU 410. In some embodiments, the IPG 10 continues to record data related to the current activity of the patient's heart 12 or the IPG 10. The process 500 then continues to state 508. At state 508, the IPG 10 which is connected to the RMU 410 transmits the notification of the high risk or emergency event determined at decision state 504 to the RMU 410.

The IPG 10 then proceeds to perform a full download of the data stored in the memory 94 of the IPG 10 to the RMU 410. In some embodiments, all of the data stored in the memory 94 is downloaded by the RMU 410 during a full download. In other embodiments, only data related to the changed data or a significant event is downloaded. In some embodiments, the data to be downloaded is determined based on one or more indicators or flags 123. Process 500 continues from state 513 to state 514 where the flag of the event flag module 123 is reset. The set flag indicates in some embodiments that a full data download has occurred, and that no major events have occurred since that time.

Returning to decision state 502, if no recordable event is detected, then the process 500 continues to decision state 509. At decision state 509 it is determined whether or not a scheduled download should occur. A scheduled download may be determined by the IPG 10 or by the RMU 10. In some embodiments, an external programmer 102 is used by a physician to program a download schedule into the memory 94 of the IPG 10. In some embodiments, a download schedule is maintained by the RMU 410 and the IPG 10 determines at decision state 509 whether a scheduled download should occur based upon whether or not a query has been received from the RMU 410. If no scheduled download should occur, then the process 500 returns to state 501 and continues sensing monitored heart and device activity. Of course, in some embodiments, the IPG 10 continues to monitor heart and device activity throughout the process 500 for all the steps recited herein. If a download is determined to be scheduled at decision state 509, then the process 500 continues to decision state 510.

At decision state 510 it is determined whether or not a significant change in stored data has occurred. The IPG 10 may determine whether significant change in data has occurred by analyzing data stored in memory 94 of the IPG 10. The data stored in memory 94 may be compared and analyzed, based upon, for example, criteria programmed by a physician using an external programmer 102. For example, a significant change in stored data may be determined to have occurred if a certain number of events have occurred. In some embodiments, IPG 10 may determine whether certain threshold values for a heart rate or other sensed data have been crossed in order to determine whether significant change in stored data has occurred. If no significant change in stored data has occurred since the previous download, then the process 500 returns to state 501 and the IPG 10 continues to monitor heart and device activity. If a significant change in stored data has occurred at decision state 510, then the process 500 continues to decision state 511.

At decision state 511 it is determined whether or not the IPG 10 is connected to RMU 410. As explained with respect to decision state 506 above, this step comprises determining whether or not the RMU 410 is in range and the communication link 104 has been established. If no such link 104 has been established at decision state 511, then the process 500 continues to state 512. If a link 104 has been established, then the process 500 continues to state 513. At 512, the process 500 waits and attempts to connect the IPG 10 with the RMU 410.

When the IPG 10 is connected with the RMU 410 at state 511 or 512, then the process 500 continues to state 513 where a full interrogation or download occurs. Sensed data stored in memory 94 of the IPG 10 is transmitted to the RMU 410 as described above. In some embodiments, all of the data stored in memory 94 of the IPG 10 is transmitted to the RMU 410. In some embodiments, sensed data is transmitted to the RMU 410 but certain other data including configuration data and settings are not transmitted to the RMU 410. In some embodiments, the data transmitted to the RMU 410 is determined in part based upon whether a high risk event has occurred or whether a significant change has occurred, as well as the specific sensed data corresponding to the events or changes. For example, if multiple flags are used with the IPG 10, then the data downloaded from memory 94 may be determined in part based upon which flags are disabled.

The process 500 then continues to state 514 where the flag of event flag module 123 is reset. The reset flag indicates the data in memory 94 has been downloaded by the RMU 410 since the last event has occurred. The process 500 then returns to state 501 and the IPG 10 continues to monitor heart and device activity.

Figure 6:
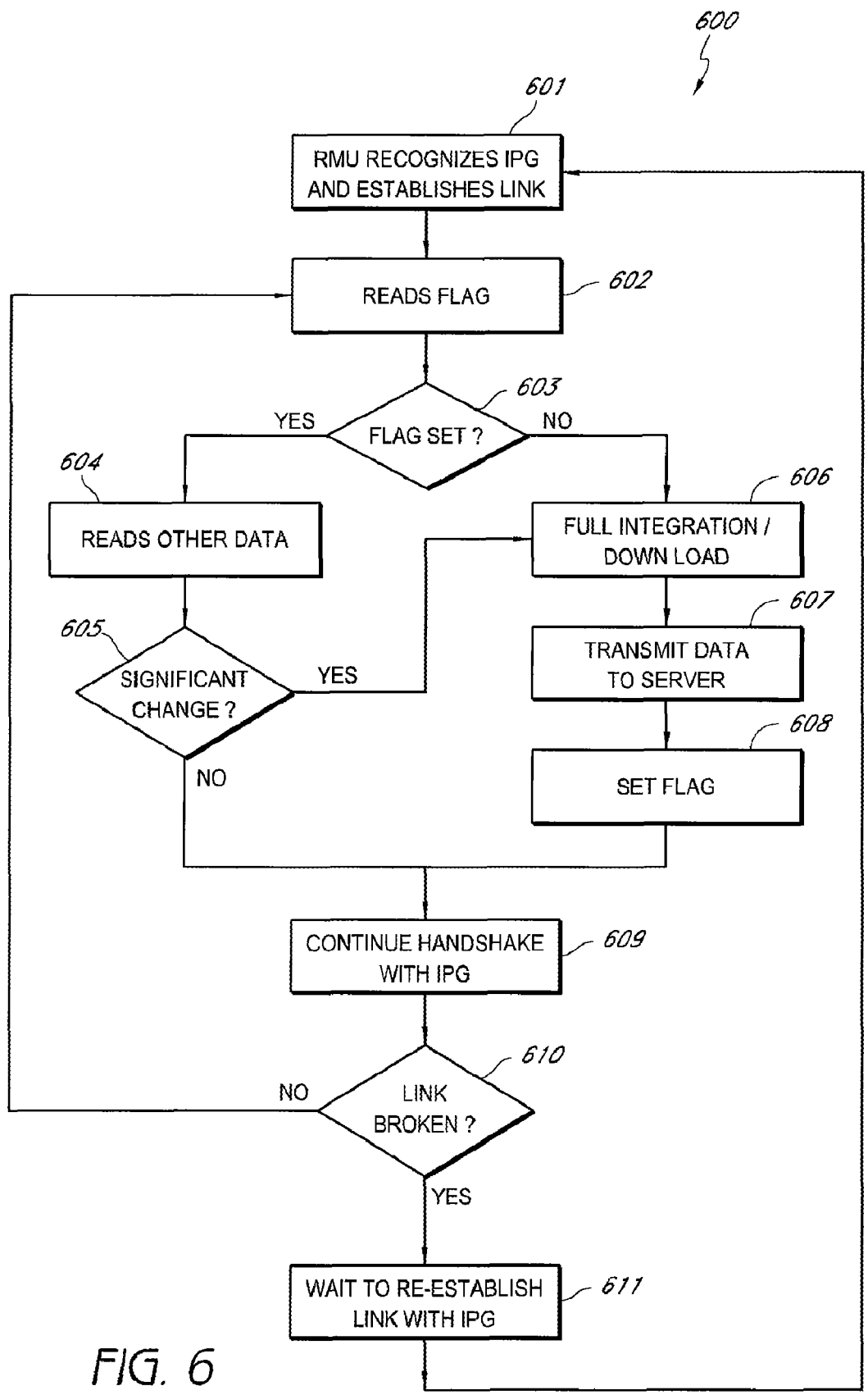
FIG. 6 is a flow chart describing a method for intelligently controlling the scheduled download of data to a remote monitoring unit based upon the occurrence of a significant event or change in stored data, according to an embodiment of the invention.

While the process 500 describes the operation of the IPG 10 according to some embodiments, the RMU 410 also may perform some of the steps shown in FIG. 5 and provide additional functionality. FIG. 6 is a flow chart describing a process 600 for the efficient monitoring of cardiac data collected by an IPG 10 according to one embodiment. The process 600 may be utilized, for example, by an RMU 410 at periodic intervals to collect data from an implanted IPG 10 when there has been a significant change in the data stored in the memory 94 of the implanted IPG 10, or when an event has occurred.

The process 600 begins at state 601 when the remote monitoring unit 410 recognizes the implanted pulse generator 10 and establishes a communications link 104. In a preferred embodiment, the RMU 410 attempts to perform the process 600 at periodic intervals, such as once each day or once each week. Of course, other periods may be set between attempted downloads according to the process 600. In the event that the IPG 10 is outside of the range of the RMU 410 or for some other reason the RMU 410 cannot open a communications channel with the IPG 10 at the scheduled time, then the RMU 410 may continue to attempt to establish contact until it is successful. The communications link 104 between the RMU 410 and the IPG 10 may comprise any type of wireless transmission, protocol such as RF transmissions, as discussed above. At state 601, the IPG 10 is in a low power consumption mode, because the IPG 10 is not transferring significant amounts of data to the RMU 410, but has merely verified its presence and opened a wireless channel with the RMU 410.

At state 602, the RMU 410 reads the flag 123 in the IPG 10. The flag 123 may be in either an enabled or disabled condition. In general, an enabled flag condition corresponds to the flag being set and indicates that no event has occurred since the previous data download by the RMU 410. A disabled flag condition indicates that between the time that the RMU 410 last downloaded data from the IPG 10, an event has occurred that triggered the microprocessor 60 of the IPG 10 to disable the flag 123. An event may comprise a medical condition in some embodiments, such as a supraventricular tachycardia, atrial fibrillation, any other arrhythmia, or some other condition that may require medical assistance. In some embodiments, an event may comprise a current or imminent device failure, such as a low battery power level in the IPG, a dislodged lead, or the like. While this state has been discussed with reference to a single flag, the IPG 10 may store multiple flags 123 corresponding to different conditions. For example, the IPG 10 may store one flag 123 related to the occurrence of a patient medical condition and another flag 123 related to the occurrence of an equipment malfunction. In some embodiments, multiple flags correspond to multiple medical conditions, such as one for a high ventricular rate episode, one corresponding to a high atrial rate episode, and any others that may be useful in distinguishing events.

At decision state 603, if the flag is set, corresponding to an enabled condition, then the process 600 continues to state 604. If the flag is not set, corresponding to a disabled condition, then the process 600 continues to state 606.

At state 604, the RMU 410 reads other data stored in the memory 94 of IPG 10. The other data read at state 604 may comprise a subset of the data stored in the memory of IPG 10. For example, the subset of data may indicate whether or not there has been significant change in the larger collection of cardiac data stored by the IPG 10. A significant change in the data stored by IPG 10 may comprise a change in the average heart rate, the occurrence of electrical stimulation therapy, or the like. The transmitting of the subset of data may require more power than only reading the flag 123, but may require substantially less power than a full download.

At decision state 605, based on the subset of data read at state 604, it is determined by the RMU 410 whether a significant change has occurred in the larger collection of cardiac data since the last download. What constitutes a significant change may be determined by a physician in some embodiments. If it is determined that a significant change has occurred, the process continues to state 606. If a significant change has not occurred, then the process continues to state 609.

The process 600 reaches state 606 if the flag 123 is not set as determined at decision state 603 or there has been significant change in the data stored in the IPG 10 as determined at decision state 605. At state 606, a full interrogation or download of the data stored in the memory 94 of the IPG 10 is performed. During state 606, the IPG may transfer data collected that is related to, for example, electrical signals generated by the heart, pulses and other therapeutic stimulation provided by the IPG 10, impedance measurements sensed by the IPG 10, or the like. In some embodiments utilizing multiple flags 123, having one flag 123 that is in a disabled condition may initialize a full download. In some embodiments, having less than all of the flags 123 in a disabled condition may cause the RMU 410 to download data related to the events indicated by any of the flags 123 in a disabled condition, but not to download data related to the flags 123 in an enabled condition. A download at state 606 represents a high power consumption mode for the IPG 10, and therefore some embodiments of the current invention allow for the efficient use of this process by downloading the full set of data only when it is necessary, rather than at every scheduled period.

After data has been downloaded to the RMU 410, the process 600 continues to state 607. At state 607, the RMU 410 may transmit data collected during the download process to server 420. In some embodiments, server 420 may store a collection of medical data and may be accessible by a monitoring station 430 located at a medical facility 445 through a network 450. In some embodiments, the data downloaded at state 606 and transmitted to the server 420 at state 607 is read by the server 420 to determine if the data indicates an event requiring an alarm or other notification be sent to a physician 440 or any other emergency technician at the medical facility 445. If it is determined that a condition exists warranting an alarm be sent, then alarm data is transferred to the monitoring station 430 and is displayed to a physician or clinician 440 at that location. The alarm data may induce the monitoring station to sound an audio alarm, display a visual alarm or message, or the like. In some embodiments, an alarm may comprise an e-mail, SMS text message, voice message sent electronically or over an automated telephone system, pager, fax, or the like. In some embodiments, the server 420 may continue to send an alarm until an acknowledgement is received such as by return e-mail or SMS text message.

In some embodiments, an alarm may be provided on the RMU 410 itself. This may be beneficial, for example, where a patient 400 is living with a care provider. In this case, the alarm, whether it is an audio alarm or visual alarm, may alert a care provider to the patient's condition and possible need for assistance. In some embodiments, an error code determined by analyzing the data downloaded from the IPG 10 is used to determine a specific alarm output by the RMU 410. In some embodiments, this error code may be transmitted with the data at state 607.

The process 600 continues at state 608, where the flag 123 in the IPG 10 is set by the RMU 410. The flag 123 indicates that the data contained in the IPG 10 has been downloaded. With the flag in an enabled condition, as set at state 608, the RMU 410 will not download data from the IPG 10 until the next scheduled download period, and then only if significant change in the data has occurred. State 608 is shown occurring after state 607. However, in some embodiments, state 608 may occur substantially simultaneously with state 607 or before state 607. Once the data has been transmitted to the RMU 410 at state 606, and the flag has been set at state 608, then the IPG 10 returns to a low power state because it is no longer transferring the collected data. The process 600 then continues to state 609.

At state 609, the RMU 410 continues to maintain a communications link 104 with the IPG 10. This link 104 may be maintained as long as the IPG 10 is within the wireless communications range of the RMU 410. In some embodiments, this communications channel is only maintained as long as a predetermined percentage of data transfer attempts are successful in order to avoid the need to use battery life retransmitting previously sent data that was lost during transmission. When the IPG 10 is in range, maintaining the handshake with the IPG requires only a low power consumption and allows the RMU 410 to maintain efficient contact with the IPG 10.

The process 600 next continues to decision state 610. At decision state 610, it is determined whether the established communication link 104 between the RMU 410 and the IPG 10 has been broken. If it is determined that the link 104 has not been broken, then the process 600 returns to state 602 and reads the flag 123 of the IPG 10 at the next scheduled download. If it is determined that the communications link between the RMU and the IPG 10 has been broken at state 610, then the RMU waits to reestablish the communication link 104 with the IPG at state 611. When it is determined at state 611 that the communications link 104 with the IPG can be reestablished, then the process returns to state 601.

The process 600 described above therefore allows for the efficient periodic download of data stored on IPG 10 to a remote monitoring unit 410. Downloads occur at a periodic interval, but only on the condition that a flag has been disabled indicating that an event has occurred, or if there has been a significant change in the stored data. Thus, data indicating the continued normal operation of the IPG 10 is not downloaded. This allows the IPG 10 to transmit data stored in memory 94 only when necessary. This, in turn, preserves the battery life of the IPG 10 because power is not wasted broadcasting unnecessary information.

Figure 7:
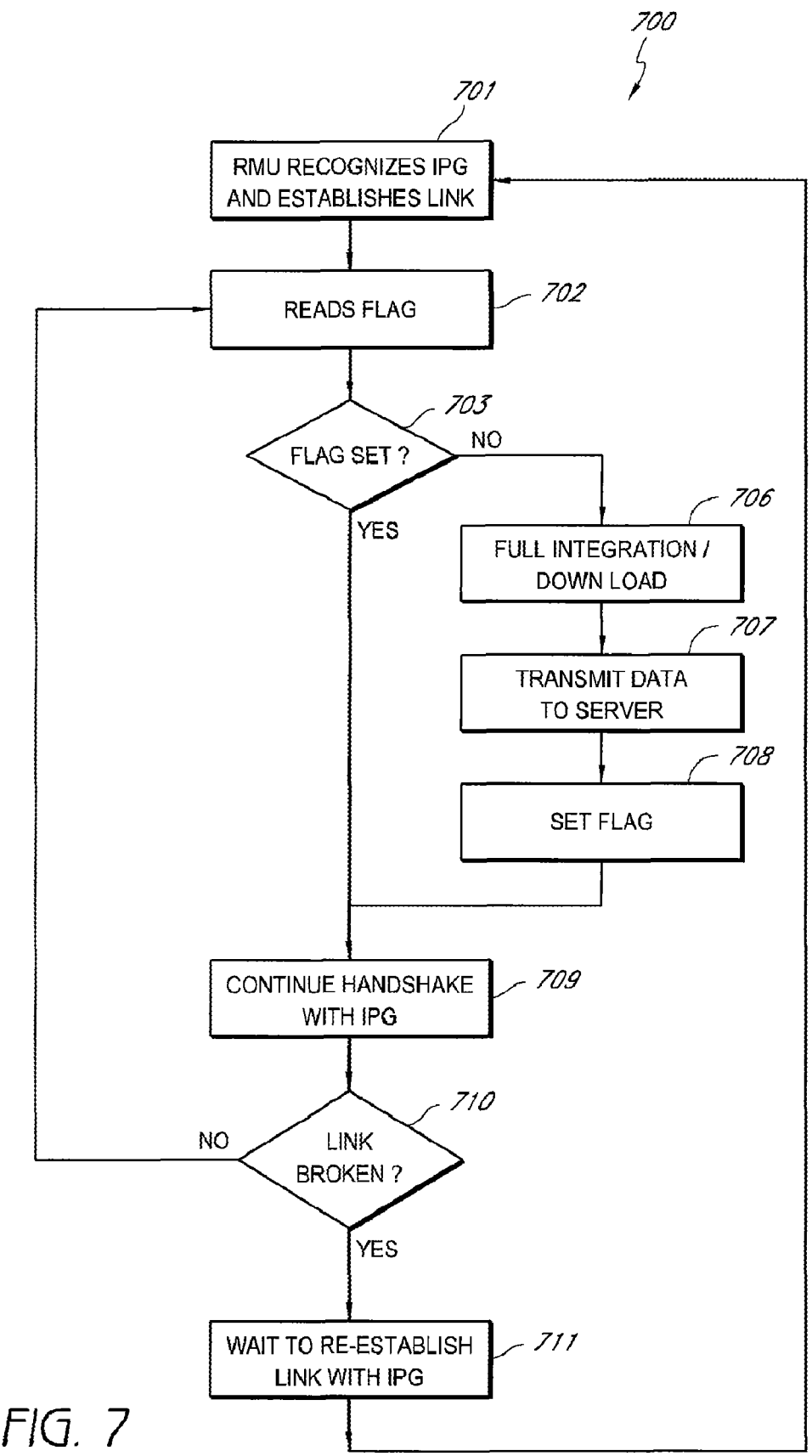
FIG. 7 is a flow chart describing a method for intelligently controlling the download of data to a remote monitoring unit based upon the occurrence of a significant event, according to an embodiment of the invention.

FIG. 7 shows an embodiment of a process 700 for downloading information stored in the IPG 10 when an event occurs between the scheduled download times. The process 700 advantageously allows for the nearly immediate download of data after an event has occurred if the IPG 10 is in range of the RMU 410.

The process 700 begins at state 701, where the RMU 410 recognizes the IPG 10 and establishes a communications link 104. The link 104 may be established, for example, when the patient enters an area within the broadcasting range of the RMU 410. For example, this range may correspond approximately with the patient's home. In some embodiments, multiple RMUs 410 may be located at different locations including a home, office, coffee shop, or the like. After a link has been established in state 701, the process continues to state 702.

At state 702, the RMU 410 reads flag 123 of the IPG 10. As discussed in more detail above with respect to process 600, in some embodiments multiple flags 123 may be stored in the IPG 10 and read by RMU 410. When multiple flags 123 are used, any or some combination of the flags 123 being disabled may trigger a complete download. In some embodiments, each of the multiple flags 123 may correspond to a type of event and determine whether data stored by IPG 10 related to that event is downloaded. If it is determined at state 703 that the flag 123 is set corresponding to an enabled condition, then the process continues to state 709 without performing any download of data. If it is determined at state 703 that the flag 123 is not set, corresponding to a disabled condition, then the process 700 continues to state 706 and a full interrogation or download is performed. At state 706, the sensed data indicative of cardiac activity or device performance or condition and stored in the memory 94 of the IPG 10 is transferred from the IPG 10 to the RMU 410.

At state 707, the RMU 410 transmits the data collected from the IPG 10 to server 420. Server 420 may determine that an alarm should be sent to medical facility 445 indicating that an event has occurred, such as a patient medical condition or a device malfunction. An alarm may be provided on monitoring station 430 to indicate to a physician 440 or other emergency medical technician that patient 400 may need assistance. An alarm may additionally be provided on RMU 410 indicating an event in some embodiments. As discussed in more detail above, an alarm may be provided at the medical facility 445, the RMU 410, or be sent by some other method to a physician 440.

At state 708, the flag 123 is set in the IPG 10. The set flag indicates that the data stored in the IPG 10 has been downloaded by the RMU 410. Thus, when an event occurs, the flag 123, having been disabled by the IPG 10, will indicate to the RMU 410 that a download is necessary. At state 708, after a download has occurred and the information related to the event has been obtained by the RMU 410, then the flag 123 will again be set indicating that no further download is necessary at that time. In this way, the amount of energy used to transmit information from the IPG 10 to the RMU 410 is reduced while allowing for a quick emergency response. In this embodiment, only the information that needs to be transferred is transferred, but that information is transferred as soon as it is needed.

If the flag is set at state 703, or after the flag is set by the RMU 410 at state 708, the process 700 continues to state 709. At state 709, the RMU 410 continues the communications link 104 and handshake protocol established at state 701 with the IPG 10.

At decision state 710, if it is determined that the link 104 has not been broken, then the process 700 returns to state 702 and reads the flag. In some embodiments, this may entail a short wait that is not likely to endanger the patient 400. For example, the RMU 410 may wait five minutes, one minute, or less than a minute between attempts to read the flag 123. This process 700 may occur in some embodiments as long as the IPG 10 is within range of the transmitter of the RMU 410. If it is determined at state 710 that the link 104 has been broken, then the process continues to state 711 where the RMU waits to reestablish the communications link with the IPG 10. When the IPG 10 is again detected, the process 700 returns to state 701 and establishes the link 104. Thus, according to this embodiment, whenever the RMU 410 is in range of the IPG 10, a communications link 104 is established. If an event occurs while a communications link 104 is established, such as a medical emergency or a device failure, then the IPG 10 disables a flag condition, causing the RMU 410 to determine that data should be downloaded from the IPG 10.

As can be seen, various embodiments described herein provide a number of advantages over the prior art. For example, according to some embodiments of the invention, a remote monitoring unit may advantageously monitor data stored in an implanted device over periodic intervals, but only perform a full download when the data has changed significantly. This may allow for the more efficient use of the implanted device battery and longer device life span. According to some embodiments of the invention, a remote monitoring unit may continually be in contact and in communication with an IPG whenever the IPG is within range of the RMU. Advantageously, the IPG may operate in a low power state during this communication while it is not downloading or transferring any information from the device memory to the RMU. Only when an event occurs and the IPG sets a flag will a data download be initiated. Thus, the system advantageously allows for the nearly immediate download of data related to the occurrence of a significant event, such as a medical emergency or device failure. It will be understood that not all of the advantages described herein may be achieved in each embodiment of the invention. Furthermore, advantages not specifically discussed may nonetheless be achieved by some embodiments as taught herein. Nonetheless, those embodiments may be practiced without departing from the spirit of the invention. An artisan of ordinary skill will also understand that while reference is made to the monitoring of cardiac activity by an IPG, other implantable devices that sense other aspects of a patient's medical condition and transmit sensed data to a monitoring computer may be utilized in order to accomplish certain advantages described herein without departing from the scope of the invention. For example, certain aspects disclosed herein may be utilized with implantable glucose monitors, or the like.

The methods and steps described herein describe particular embodiments, and are not limiting. An artisan of ordinary skill will understand that certain steps described herein may be removed or performed in a different order, and other steps not described may be added. Furthermore, the steps are generally described as being performed by a remote monitoring unit, but certain steps may be implemented utilizing either hardware components or software instructions in any computing device.

What is claimed is:

1. A system, comprising:
    an implantable medical device comprising a memory and at least one sensor, the implantable medical device configured to sense data indicative of a patient's medical condition and the performance of the implantable medical device, and configured to store the data in the memory as a full set of data, the memory of the implantable medical device configured to store an indicator configured to be placed in an enabled condition or a disabled condition by a processor of the implantable medical device, the implantable medical device further comprising a wireless transceiver configured to send and receive data,
    an external monitoring unit comprising a wireless transceiver configured to send data to and receive data from the implantable medical device, the external monitoring unit configured to poll the implantable medical device to determine whether the indicator is in an enabled or disabled condition and to:
        when the indicator is in a disabled condition, initiate a download of the full set of data and induce the implantable medical device to place the indicator in an enabled condition following a download;
        when the indicator is in an enabled condition, initiate a download of a subset of the full set of data, process the subset of data to determine whether the data corresponds to a significant change since a previous download based on a plurality of pre-selected criteria, and initiate a download of the full set of data when there has been a significant change, and
    a server connected to the external monitoring unit over a network comprising a database, the server configured to receive the data indicative of the patient's medical condition and the performance of the implantable medical device and store the data in the database, the server further configured to allow access to the data indicative of the patient's medical condition and the performance of the implantable medical device by a networked medical computer station.

2. The system of claim 1, wherein the processor is configured to determine whether the sensed data corresponds to an occurrence of an event based on a plurality of pre-selected criteria, and wherein the processor is configured to place the indicator in the disabled condition when the sensed data corresponds to the occurrence of an event.

3. The system of claim 2, wherein the event comprises at least one of an equipment malfunction, a low battery charge reading, and a dangerous medical condition.

4. The system of claim 2, wherein the event comprises at least one sensed medical condition selected from the group of ventricular fibrillation, ventricular tachycardia, atrial fibrillation, and atrial flutter.

5. The system of claim 1, wherein the database is configured to store data from a plurality of additional implantable medical devices.

6. The system of claim 1, wherein the server is further configured to analyze the data indicative of the patient's medical condition and generate an alarm based on a plurality of pre-selected criteria.

7. The system of claim 6, wherein the alarm comprises at least one of a visual indicator, an audio indicator, an e-mail, an SMS text message, a telephone message, and a page.

8. The system of claim 1, wherein the external monitoring unit is configured to poll the implantable medical device according to a download schedule comprising a plurality of scheduled downloads.

9. The system of claim 8, wherein the external monitoring unit is configured to analyze a subset of the data indicative of the patient's medical condition and the performance of the implantable medical device and to inhibit one of the scheduled downloads if the data does not correspond to a significant change based on a plurality of pre-selected criteria.

10. The system of claim 1, wherein the pre-selected criteria correspond to at least one of a number of detected events, a threshold heart rate, a detected heart arrhythmia, an expected battery lifespan, and an expected device performance criteria.

11. The system of claim 1 wherein the memory of the implantable medical device is configured to store a plurality of indicators, each configured to be placed in an enabled condition or a disabled condition by the processor and each corresponding to different associated data indicative of a patient's medical condition and the performance of the implantable medical device.

12. The system of claim 11, wherein one of the plurality of indicators corresponds to medical conditions.

13. The system of claim 11, wherein one of the plurality of indicators corresponds to device conditions.

* * * * *